United States Patent [19]
Riviere et al.

[11] Patent Number: 5,540,654
[45] Date of Patent: Jul. 30, 1996

[54] IONTOPHORETIC ELECTRODE

[75] Inventors: Jim E. Riviere, Raleigh; Richard A. Rogers, Garner; Nancy A. Monteiro-Riviere, Raleigh, all of N.C.

[73] Assignee: North Carolina State University, Raleigh, N.C.

[21] Appl. No.: 300,054

[22] Filed: Sep. 2, 1994

[51] Int. Cl.$^6$ ..................................................... A61N 1/30
[52] U.S. Cl. ........................................................ 604/20
[58] Field of Search ............................... 604/20, 19, 49; 128/731; 607/152

[56] References Cited

U.S. PATENT DOCUMENTS

| | | | |
|---|---|---|---|
| 3,991,755 | 11/1976 | Vernon et al. | 128/172.1 |
| 4,308,873 | 1/1982 | Maynard | 128/731 |
| 4,406,658 | 9/1983 | Lattin et al. | 604/20 |
| 4,474,570 | 10/1984 | Ariura et al. | 604/20 |
| 4,702,732 | 10/1987 | Powers et al. | 604/20 |
| 4,752,285 | 6/1988 | Petelenz et al. | 604/20 |
| 4,820,263 | 4/1989 | Spevak et al. | 604/20 |
| 4,949,725 | 8/1990 | Kaviv et al. | 128/731 |
| 4,950,229 | 8/1990 | Sage, Jr. | 604/120 |
| 5,003,991 | 4/1991 | Takayana et al. | 128/784 |
| 5,023,085 | 6/1991 | Francoeur et al. | 424/449 |
| 5,038,782 | 8/1991 | Gevins et al. | 128/731 |
| 5,047,007 | 9/1991 | McNichols et al. | 604/20 |
| 5,057,072 | 10/1991 | Phipps | 604/20 |
| 5,068,226 | 11/1991 | Weinshenker et al. | 514/58 |
| 5,084,006 | 1/1992 | Lew et al. | 604/20 |
| 5,084,008 | 1/1992 | Phipps | 604/20 |
| 5,088,977 | 2/1992 | Sibalis | 604/20 |
| 5,135,480 | 8/1992 | Bannon et al. | 604/20 |
| 5,310,403 | 5/1994 | Haynes | 604/20 |
| 5,344,440 | 9/1994 | Stephen | 607/152 |

OTHER PUBLICATIONS

Bellantone, et al., Enhanced Percutaneous Absorbtion Via Iontophoresis I. Evaluation of An In Vitro System and Transphort of Model Compounds, *Intl. J. Pharm.* 30:63 (1986).

Bezzant, et al., Painless Cauterizat ion of Spider Veins With The Use of Iontophoretic Local Anesthesia, *J. Amer. Academy of Dermatology* 19(5):869 (1988).

Brown, et al., Transdermal Delivery of Drugs, *Ann. Med. Rev.* 39:221 (1988).

Gangarosa, et al., Conductivity of Drugs Used for Iontophoresis, *J. Pharm. Sci.* 67(10): 1439 (1978).

Heit, et al., Transdermal Iontophoretic Peptide Delivery: In Vitro and In Vivo Studies with Luteinizing Hormone Releasing Hormone, *J. Pharm. Sci.* 82(3):240 (1993).

Kemppainen, et al., Methods for Skin Absorption, 176 (1990).

Riviere, et al., The Isolated Perfused Porcine Skin Flap (IPPSF), *Funmdamental and Applied Toxicology*, 7:444 (1986).

Riviere, et al., The Isolated Perfused Porcine Skin Flap as an In Vitro Model for Percutaneous Absorption and Cutaneous Toxicology, *Critical Reviews in Toxicology* 21(5):329 (1991).

Sanderson, et al., Iontophoretic Delivery of Nonpeptide Drugs: Formulation Optimization for Maximum Skin Permeability, *J. Pharm. Sci.* 78(5):361 (1989).

*Primary Examiner*—Manuel Mendez
*Attorney, Agent, or Firm*—Bell, Seltzer, Park & Gibson

[57] ABSTRACT

The iontophoretic device of the present invention comprises (a) a source for providing an electrical signal, (b) an electrode mounting block having a plurality of separate openings formed therein in spaced-apart relation from one another, with each of the openings configured to receive an iontophoresis electrode, (c) a plurality of iontophoresis electrodes electrically connected to the source and capable of transmitting electrical signal, each of the iontophoresis electrodes having a skin contact surface and each of the iontophoresis electrodes being received in one of the openings formed in the electrode mounting block, (d) a signal distribution network electrically connected to both the source and each of the plurality of electrodes and configured for distributing a electrical signal to each of the plurality of electrodes, and (e) a receiver connected to the source for accepting electrical signal transmitted by the plurality of electrodes, with the receiver of sufficient capacity to simultaneously accept electrical signal transmitted by each of the plurality of electrodes.

28 Claims, 1 Drawing Sheet

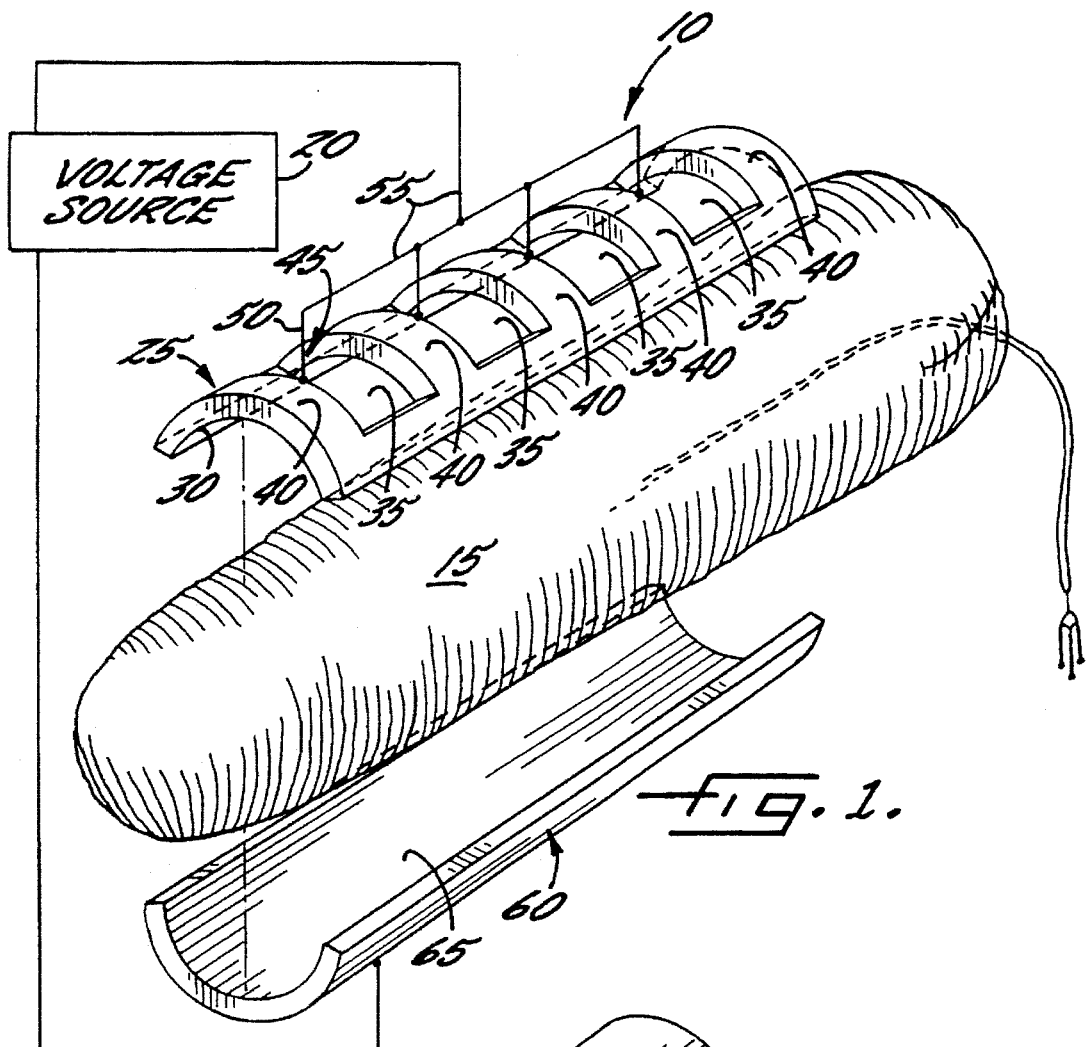
fig. 1.
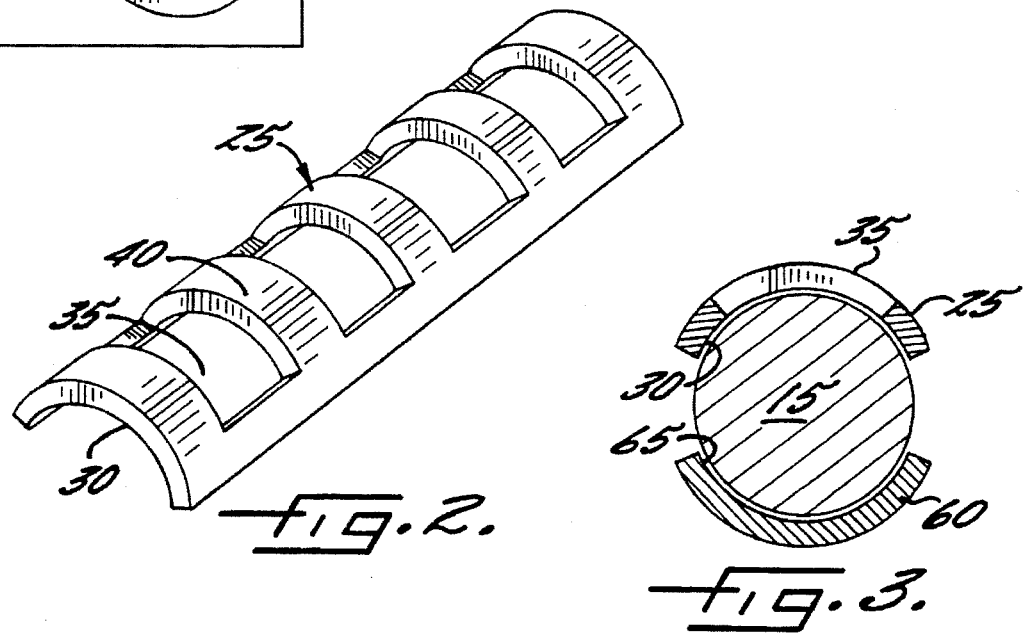
fig. 2.
fig. 3.

IONTOPHORETIC ELECTRODE

FIELD OF THE INVENTION

The present invention relates to electrically assisted transdermal absorption (i.e., iontophoresis), and particularly to a novel iontophoretic device.

BACKGROUND OF THE INVENTION

Transdermal delivery techniques which utilize electrical signal for delivering a drug to a patient for systemic distribution by blood flow are well known. In particular, iontophoretic techniques have demonstrated utility in the transdermal delivery of ions of soluble salts, including peptides.

Since the introduction of the isolated perfused porcine skin flap (IPPSF), iontophoretic studies of drug penetration, absorption and toxicity have received increasing attention. However, the major limitation of utilizing IPPSF in iontophoretic studies is that only single test compounds can be evaluated in a single IPPSF according to conventional techniques. The cost of performing extensive iontophoretic evaluations of multiple compounds is prohibitively large due to the costs incident in the procurement and preparation of multiple IPPSFs. At present, no alternative in vitro model system is available, and moral considerations limit the desirability of evaluating drug penetration, absorption and particularly toxicity in vivo. As a result, there is a need in the art for a method of efficiently and cost-effectively evaluating the penetration, absorption, and toxicity of a multiplicity of compositions using a single iontophoretic device. Previously, it was believed that the simultaneous iontophoretic delivery of a multiplicity of compounds by adjacent electrodes would not be possible due to electrical and chemical interference from adjacent electrodes.

Accordingly, it is an object of the present invention to provide an iontophoretic device useful for evaluating the penetration, absorption, and toxicity of compositions by iontophoresis. It is a further object of the present invention to provide an iontophoretic device useful for evaluating a multiplicity of compositions using iontophoresis.

SUMMARY OF THE INVENTION

Accordingly, it is an object of the present invention to provide an iontophoretic device useful for evaluating the penetration, absorption, and toxicity of compositions by iontophoresis. It is a further object of the present invention to provide an iontophoretic device useful for evaluating a multiplicity of compositions using iontophoresis.

The iontophoretic device of the present invention comprises (a) a source for providing an electrical signal, (b) an electrode mounting block, (c) a plurality of iontophoresis electrodes electrically connected to the source and capable of transmitting an electrical signal, each of which have a skin contact surface, (d) a signal distribution network connected to the source and the electrode, and (e) a receiver connected to the source. The mounting block typically has a plurality of separate openings formed therein in spaced-apart relation from one another. Each of the openings are configured to receive an iontophoresis electrode. Accordingly, each of the iontophoresis electrodes are received in one of the openings formed in the electrode mounting block. The signal distribution network is electrically connected to both the source and each of the plurality of electrodes, and is capable of distributing an electrical signal to each of the plurality of electrodes. The provision of electrical signal to each of the plurality of electrodes causes the iontophoretic delivery of ions through the skin with which the electrodes are in contact. The receiver accepts electrical signal transmitted by the plurality of electrodes, and typically has sufficient capacity to simultaneously accept electrical signal transmitted by each of the plurality of electrodes, thus permitting the simultaneous evaluation of a multiplicity of compositions with a single IPPSF preparation.

The foregoing and other objects and aspects of the present invention are explained in detail in the specification set forth below.

BRIEF DESCRIPTION OF THE DRAWINGS

FIG. 1 is an exploded perspective view of an iontophoretic device in accordance with the present invention which is in contact with an isolated perfused porcine skin flap.

FIG. 2 is a perspective view of the electrode mounting block.

FIG. 3 is an assembled cross-sectional view of the iontophoretic device of the present invention in contact with an isolated perfused porcine skin flap.

DETAILED DESCRIPTION OF THE INVENTION

The iontophoretic device of the present invention is useful for evaluating compositions by iontophoretic delivery through a portion of skin. In particular, the device is useful for simultaneously evaluating a multiplicity of compositions by iontophoretic delivery through a portion of skin. Any suitable skin source known to those skilled in the art may be used. For example, the iontophoretic device of the present invention may be used to evaluate compositions iontophoretically delivered through human skin. Preferably, the skin source is mammalian skin, particularly porcine skin. More preferably, the skin source is an isolated perfused porcine skin flap prepared in accordance with the teachings of Riviere, et al. *Critical Reviews in Toxicology* 21:329 (1991), the disclosure of which is incorporated herein by reference, in its entirety.

According to FIG. 1, an iontophoretic device of the present invention is shown in contact with an isolated perfused porcine skin flap 15. The device 10 comprises (a) a source 20 for providing an electrical signal. The source 20 may be any suitable source of electrical signal, which may be in the form of current or voltage. Preferably, the source 20 provides an electrical signal in the form of current. Exemplary current sources 20 include a battery.

The device further comprises (b) an electrode mounting block 25. Typically, the electrode mounting block 25 is comprised of an electrically insulating material. Exemplary materials include plastics such as polyethylene, polypropylene, polystyrene, and polyvinyl chloride. The mounting block 25 has a skin contact surface 30. Preferably, the skin contact surface 30 conforms to the general shape of the skin source. For example, according to the embodiment shown in FIGS. 1–3, wherein the skin source is an isolated perfused porcine skin flap 15, the mounting block 25 is preferably substantially curvilinear in shape. The electrode mounting block 25 is typically adhered to the skin surface using a suitable adhesive. For example, the mounting block 25 may be adhered to the skin surface using liquid adhesive or two-sided adhesive tape.

The mounting block 25 has a plurality of separate openings 35 formed therein. The openings 35 are in spaced-apart relation from one another, and are typically separated by electrically insulating material 40. Suitable materials include those described above.

Each of the openings 35 in the mounting block 25 are configured to receive an iontophoresis electrode 45. The openings 35 may be configured according to any suitable geometric shape. For example, the openings 35 may be substantially round, rectangular, square, elliptical, oval, etc. In addition, non-regular geometric shapes may also be used. It is preferred to configure the openings 35 with a geometric shape which permits the maximum number of openings 35 in the mounting block 25. Typically, the electrode mounting block 25 has from 2 to 6 separate openings 35 formed therein. According to the embodiment shown in FIGS. 1–2, the electrode mounting block 25 has four openings 35 formed therein which are substantially square.

Sufficient electrically insulting material 40 is provided between the openings 35 of the mounting block 25 to prevent iontophoretic delivery from one electrode 45 from interfering with iontophoretic delivery by an adjacent electrode 45. The amount of electrically insulating material 40 between the electrode 45 will depend on the compounds to be delivered, the size of the openings 35, and the electrical delivery conditions, and can be readily determined by one skilled in the art. Typically, the openings 35 are separated by between about 0.5 cm or 1 cm to about 5 or 10 cm or even to about 1 or 2 meters, of electrically insulating material 40.

The iontophoretic device 10 further comprises (c) a plurality of iontophoresis electrodes 45. The iontophoresis electrodes 45 are electrically connected to the source 20 such that the source 20 provides an electrical signal to each of the electrodes 45. Each of the iontophoresis electrodes 45 also has a skin contact surface. The skin contact surface preferably conforms substantially to the shape of the skin source. For example, according to the embodiment shown in FIG. 1, wherein the skin source is an isolated perfused porcine skin flap 15, the electrodes 45 are preferably substantially curvilinear in shape. Each of the plurality of electrodes 45 is received in one of the plurality of openings 35 formed in the electrode mounting block 25.

The iontophoretic electrodes 45 may comprise any suitable electrode system known to those skilled in the art. Typically, the electrodes 45 comprise an electrode matrix (not shown) containing the test composition to be delivered, and a metal conductor 50. Typically, the electrode matrix is placed in the opening 35 in the electrode mounting block 25, and the conductor 50 is placed in contact therewith. The conductor is electrically connected at its opposite end to the signal distribution network 55.

The electrode matrix can be any suitable material known to those skilled in the art, which is biocompatible with human skin, which is capable of conducting the electrical signal, and which is capable of maintaining the test composition in a mobile state for delivery to the skin. Suitable electrode matrices which can be placed in the opening 35 of the electrode mounting block 25 include but are not limited to hydrophilic gels such as agar gel, karaya gum gel, gelatin, cellulose, carboxyvinyl based gel or polyacrylamide based gel; pastes; suspensions; solutions; tapes; patches; natural or polymeric porous matrices such as POREX™; or the like.

Typically, each of the electrodes 45 contains a different test composition, or a different concentration of the same test composition, such that a multiplicity of test compositions may be evaluated simultaneously. The test composition may be any composition desirously evaluated using iontophoretic delivery. Typically, the test composition is a medicament, and each of the plurality of electrodes 45 contains a different medicament, or a different concentration of the same medicament. The evaluation is accomplished by assessing medicament concentrations in a biopsy under each electrode 45, or by independently assaying medicament flux in venous perfusates. Irritation is assessed by histological or toxicological examination of the biopsies.

The iontophoretic device further 10 comprises (d) signal distribution network 55 electrically connected to both the source 20 and each of the plurality of electrodes 45. The signal distribution network 55 distributes an electrical signal to each of the plurality of electrodes 45. Typically, the signal distribution network 55 is comprised of electrically conducting material. Suitable electrically conducting materials include metals, such as for example, silver, and platinum.

According to one embodiment, the iontophoretic device further comprises a signal regulator (not shown) connected to the signal distribution network 55. The signal regulator is capable of controlling the amount of electrical signal distributed to each of the plurality of electrodes 45.

The iontophoretic device 10 further comprises (e) a receiver 60 for completing the electrical circuit. The receiver 60 is electrically connected to the source 20, and is capable of accepting electrical signal transmitted by each of the plurality of electrodes 45. According to a preferred embodiment, the receiver 60 is of sufficient capacity to simultaneously accept electrical signal transmitted by each of the plurality of electrodes 45. For example, it is preferred that the receiver 60 has sufficient surface area such that it is capable of receiving electrical signal transmitted by each of the plurality of electrodes 45. The receiver 60 serves the added function of avoiding electrical irritation by completing the electrical circuit. The receiver 60 has a skin contact surface 65. Preferably, the skin contact surface 65 conforms to the general shape of the skin source. For example, according to the embodiment shown in FIG. 1, wherein the skin source is an isolated perfused porcine skin flap 15, the skin contact surface 65 of the receiver 60 is preferably substantially curvilinear in shape.

The following examples are provided to illustrate the present invention, and should not be construed as limiting thereof. In these examples, mL means milliliters, mM means millimolar, $^{125}$I-LHRH means iodine 125 luteinizing hormone releasing hormone, $^{3}$H-LHRH means deuterated luteinizing hormone releasing hormone, MES means 2-(N-morphorino)ethane sulfonic acid, and NBF means neutral buffered formalin.

EXAMPLE 1

Method of Evaluating Multiple Drug Preparations

An isolated perfused porcine skin flap is prepared in accordance with the teachings of Riviere, et al. *Critical Reviews in Toxicology* 21:329 (1991). After harvest, the flaps are perfused at a rate of 1.0 mL/min. for one hour prior to dosing. Arterial perfusate (1.0 mL) and venous perfusate (2.5 mL) are collected at 30 and 60 minutes. The venous perfusate is initially dispensed into a polystyrene tube from which 1 mL is aliquoted into a polypropylene tube and immediately assayed for $^{125}$I-LHRH and is subsequently frozen until assayed for $^{3}$H-LHRH. The remaining sample is reserved for glucose evaluation and as a backup for $^3$H-LHRH evaluation. The arterial sample is used for glucose evaluation.

Four iontophoresis electrodes of silver mesh wire are adhered to the skin flap using TEGADERM™ adhesive tape. The indifferent cathode is approximately 1 cm×4 cm and is capable of accepting current transmitted by each of the four anodes simultaneously. The cathode is a silver-silver chloride mesh wire and is dosed with a 15.9 g/100 mL solution of saline. During each of two 30 minute dosing periods, two electrodes are dosed with either $^3$H-LHRH or $^{125}$I-LHRH in 154 mM sodium chloride and 10 mM MES. During the dosing, or drug delivery period, the iontophoretic current density is 0.4 mAmp/cm$^2$.

Following the first drug delivery period, the electrodes are subject to a three hour washout period, during which no current is transferred to the electrodes.

After the initial washout period, a second thirty minute dosing period is conducted as described above. At the termination of the second dosing period, a second three-hour washout period is carried out.

Arterial samples (1.0 mL) are collected every hour for glucose evaluation. Venous samples (2 mL) are collected at 5, 10, 15, 30, 45, 60, 75, 90, 105, 120, 135, 150, 180, 210, 215, 220, 225, 240, 255, 270, 285, 300, 315, 330, 345, 360, 390, and 420 minutes. The venous samples are analyzed as described above. This allows for the simultaneous evaluation of $^3$H-LHRH and $^{125}$I-LHRH deliveries out of different electrodes in the same IPPSF preparation.

At the termination of perfusion, a final flap weight is measured and skin samples are collected from under each active electrode in NBF for histological examination.

The foregoing is illustrative of the present invention and is not to be construed as limiting thereof. The invention is defined by the following claims, with equivalents of the claims to be included therein.

That which is claimed is:

1. An iontophoretic device comprising:
    (a) a source for providing an electrical signal;
    (b) an electrode mounting block having a plurality of separate openings formed therein in spaced-apart relation from one another, with each of said openings configured to receive an iontophoresis electrode;
    (c) a plurality of iontophoresis electrodes electrically connectied to said source and capable of transmitting an electrical signal, each of said iontophoresis electrodes comprising an electrode matrix for containing a test composition to be delivered, and having a skin contact surface and each of said iontophoresis electrodes being received in one of said openings formed in said electrode mounting block;
    (d) a signal distribution network electrically connected to both said source and each of said plurality of electrodes and configured for distributing an electrical signal to each of said plurality of electrodes; and
    (e) a receiver connected to said source for accepting electrical signal transmitted by said plurality of electrodes, with said receiver of sufficient capacity to simultaneously accept electrical signal transmitted by each of said plurality of electrodes.

2. An iontophoretic device according to claim 1, wherein said source is a battery.

3. An iontophoretic device according to claim 1, wherein said electrode mounting block is comprised of an electrically insulating material.

4. An iontophoretic device according to claim 1, wherein said electrode mounting block comprises a plurality of separate openings in spaced-apart relation from one another, having electrically insulating material therebetween.

5. An iontophoretic device according to claim 1, wherein said electrode mounting block comprises from 2 to 6 openings.

6. An iontophoretic device according to claim 1, wherein said plurality of electrodes are in contact with a medicament to be iontophoretically delivered.

7. An iontophoretic device according to claim 6, wherein the medicament is dispersed within an ionic medium.

8. An iontophoretic device according to claim 1, wherein said signal distribution network is comprised of electrically conducting material.

9. An iontophoretic device according to claim 1, wherein said signal distribution network is comprised of metal.

10. An iontophoretic device according to claim 1, wherein said signal distribution network comprises a metal selected from the group consisting of silver and platinum.

11. An iontophoretic device according to claim 1, wherein said skin contact surface of said plurality of electrodes and said receiver are substantially curvilinear in shape.

12. An iontophoretic device according to claim 1, wherein said iontophoretic device is connected to a portion of skin.

13. An iontophoretic device according to claim 12, wherein the skin to which the iontophoretic device is connected comprises an isolated perfused porcine skin flap.

14. An iontophoretic device according to claim 1 further comprising a signal regulator connected to the signal distribution network for controlling the amount of electrical signal distributed to each of said plurality of electrodes.

15. An iontophoretic device useful for simultaneously testing the delivery of a plurality of compositions, said device comprising:
    (a) a source for providing an electrical signal;
    (b) an electrode mounting block having a plurality of separate openings formed therein in spaced-apart relation from one another, with each of said openings configured to receive an iontophoresis electrode;
    (c) a plurality of iontophoresis electrodes electrically connectied to said source and capable of transmitting an electrical signal, each of said iontophoresis electrodes comprising an electrode matrix for containing a test composition to be delivered, and having a skin contact surface and each of said iontophoresis electrodes being received in one of said openings formed in said electrode mounting block;
    (d) a signal distribution network electrically connected to both said source and each of said plurality of electrodes and configured for distributing an electrical signal to each of said plurality of electrodes; and
    (e) a receiver connected to said source for accepting electrical signal transmitted by said plurality of electrodes, with said receiver of sufficient capacity to simultaneously accept electrical signal transmitted by each of said plurality of electrodes.

16. An iontophoretic device according to claim 15, wherein said source is a battery.

17. An iontophoretic device according to claim 15, wherein said electrode mounting block is comprised of an electrically insulating material.

18. An iontophoretic device according to claim 15, wherein said electrode mounting block comprises a plurality of separate openings in spaced-apart relation from one another, having insulating material therebetween.

19. An iontophoretic device according to claim 15, wherein said electrode mounting block comprises from 2 to 6 openings.

20. An iontophoretic device according to claim 15, wherein said plurality of electrodes are in contact with a medicament to be iontophoretically delivered.

21. An iontophoretic device according to claim 20, wherein the medicament is dispersed within an ionic medium.

22. An iontophoretic device according to claim 15, wherein said signal distribution network is comprised of electrically conducting material.

23. An iontophoretic device according to claim 15, wherein said signal distribution network is comprised of metal.

24. An iontophoretic device according to claim 15, wherein said signal distribution network comprises a metal selected from the group consisting of silver and platinum.

25. An iontophoretic device according to claim 15, wherein said skin contact surface of said plurality of electrodes and said receiver are substantially curvilinear in shape.

26. An iontophoretic device according to claim 15, wherein said iontophoretic device is connected to a portion of skin.

27. An iontophoretic device according to claim 26, wherein the skin to which the iontophoretic device is connected comprises an isolated perfused porcine skin flap.

28. An iontophoretic device according to claim 15, further comprising a signal regulator connected to the signal distribution network for controlling the amount of electrical signal distributed to each of said plurality of electrodes.

* * * * *